United States Patent [19]

Neftel

[11] Patent Number: 5,764,159
[45] Date of Patent: Jun. 9, 1998

[54] APPARATUS FOR REMOTELY MONITORING CONTROLLABLE DEVICES

[75] Inventor: Frédéric Neftel, Lausanne, Switzerland

[73] Assignee: Debiotech S.A., Switzerland

[21] Appl. No.: 693,305

[22] PCT Filed: Feb. 15, 1995

[86] PCT No.: PCT/FR95/00175

§ 371 Date: Aug. 2, 1996

§ 102(e) Date: Aug. 2, 1996

[87] PCT Pub. No.: WO95/22363

PCT Pub. Date: Aug. 24, 1995

[30] Foreign Application Priority Data

Feb. 16, 1994 [FR] France ................. 94/01747

[51] Int. Cl.$^6$ .................................................. H04Q 9/00
[52] U.S. Cl. ........................... 340/870.09; 340/825.36; 604/31; 604/65
[58] Field of Search ................ 340/870.09, 825.36; 604/65, 31, 891.1; 128/741

[56] References Cited

U.S. PATENT DOCUMENTS

| | | | |
|---|---|---|---|
| 3,767,859 | 10/1973 | Doering et al. | 179/1 H |
| 4,551,122 | 11/1985 | Zegers | 604/66 |
| 4,570,640 | 2/1986 | Barsa | 128/741 |
| 4,619,653 | 10/1986 | Fischell | 604/391.5 |
| 5,078,683 | 1/1992 | Sancoff | 604/65 |
| 5,104,374 | 4/1992 | Bishko | 604/31 |
| 5,319,363 | 6/1994 | Welsh | 340/825.36 |
| 5,376,070 | 12/1994 | Purvis | 604/31 |
| 5,429,602 | 7/1995 | Hauser | 604/65 |
| 5,573,506 | 11/1996 | Vasko | 604/65 |

FOREIGN PATENT DOCUMENTS

| | | | |
|---|---|---|---|
| 2 238 146 A | 5/1991 | United Kingdom | G08C 23/00 |
| WO 92/08207 | 5/1992 | WIPO | G06K 11/18 |
| WO 93/01574 | 1/1993 | WIPO | G08B 23/00 |

OTHER PUBLICATIONS

*Toward a Totally Integrated Hospital Information System: Infusion Pump Link to Patient Data Management System*, Subramanian et al. IEE 9th Annual Conf., Nov. 13–16, 1987.
International Search Report issued for PCT/FR95/00175.
*Written Opinion* issud for PCT/FR95/00175 dated Nov. 15, 1995.
*Notification de Transmission du Raport d'Examen Preliminaire International*, issued for PCT/FR95/00175, (an English translation will follow).
*Response A La Opinion Ecrite*, filed Dec. 19, 1995.

Primary Examiner—Brian Zimmerman
Assistant Examiner—Albert K. Wong
Attorney, Agent, or Firm—Wolf, Greenfield & Sacks, P.C.

[57] ABSTRACT

The invention relates to an installation for remote monitoring of a plurality of controllable equipment, in particular hospital equipment. Each of the equipment includes control means activated in response to a sequence of information. The installation also includes a portable control device. The portable control device includes a means for memorizing at least a portion of the control information relating to each equipment in association with information identifying the equipment, with the information sequence including information concerning the operating duration of the equipment. The portable control device further includes means for generating time information, and means for comparing the operating duration with elapsed time information and for transmitting an alarm signal as a function of the result of the comparison.

15 Claims, 3 Drawing Sheets

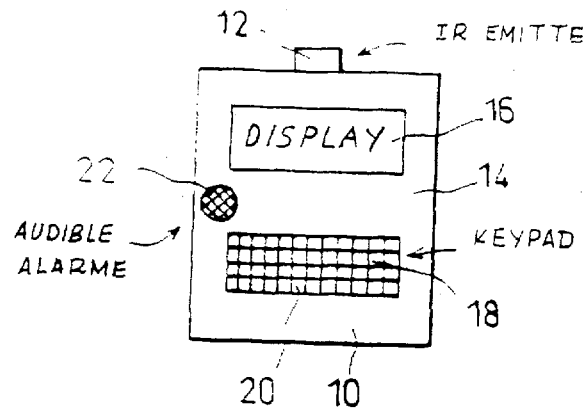
FIG_1
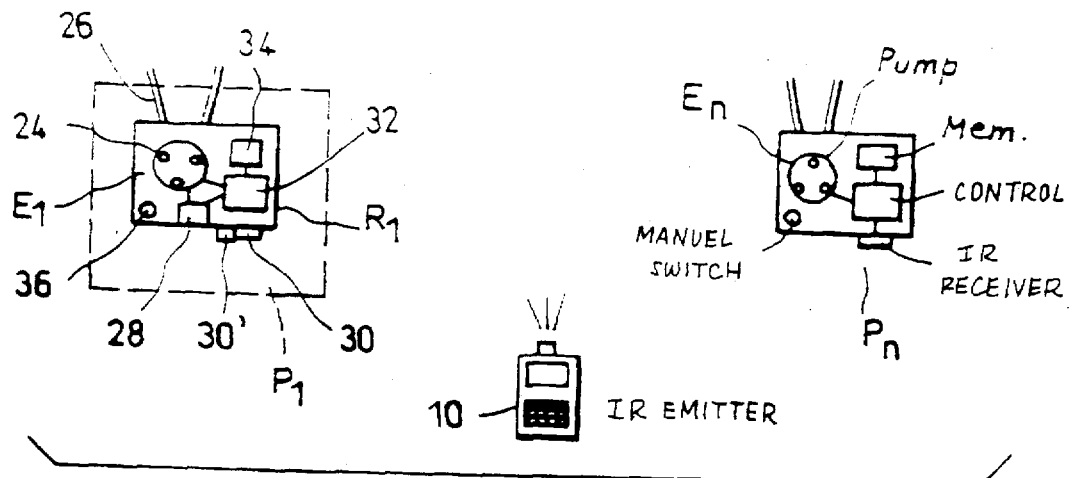
FIG_2
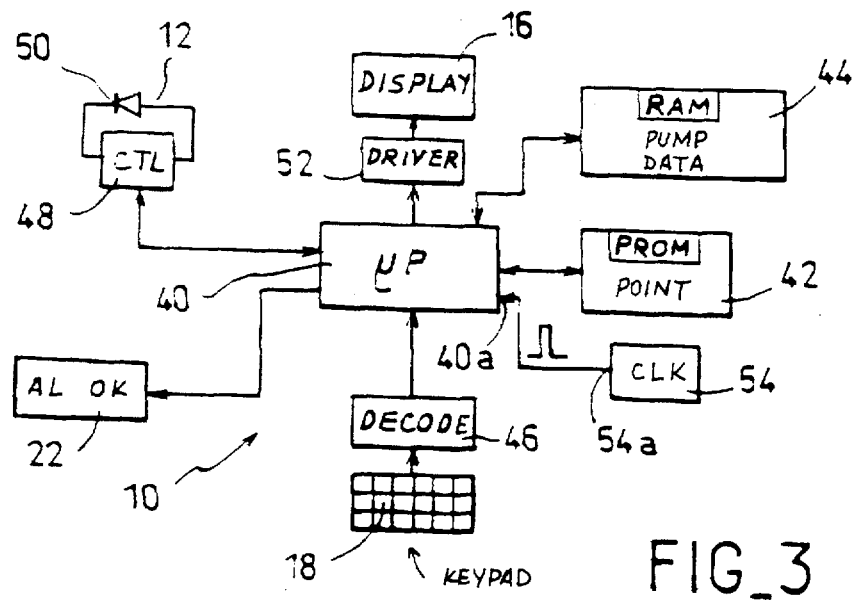
FIG_3

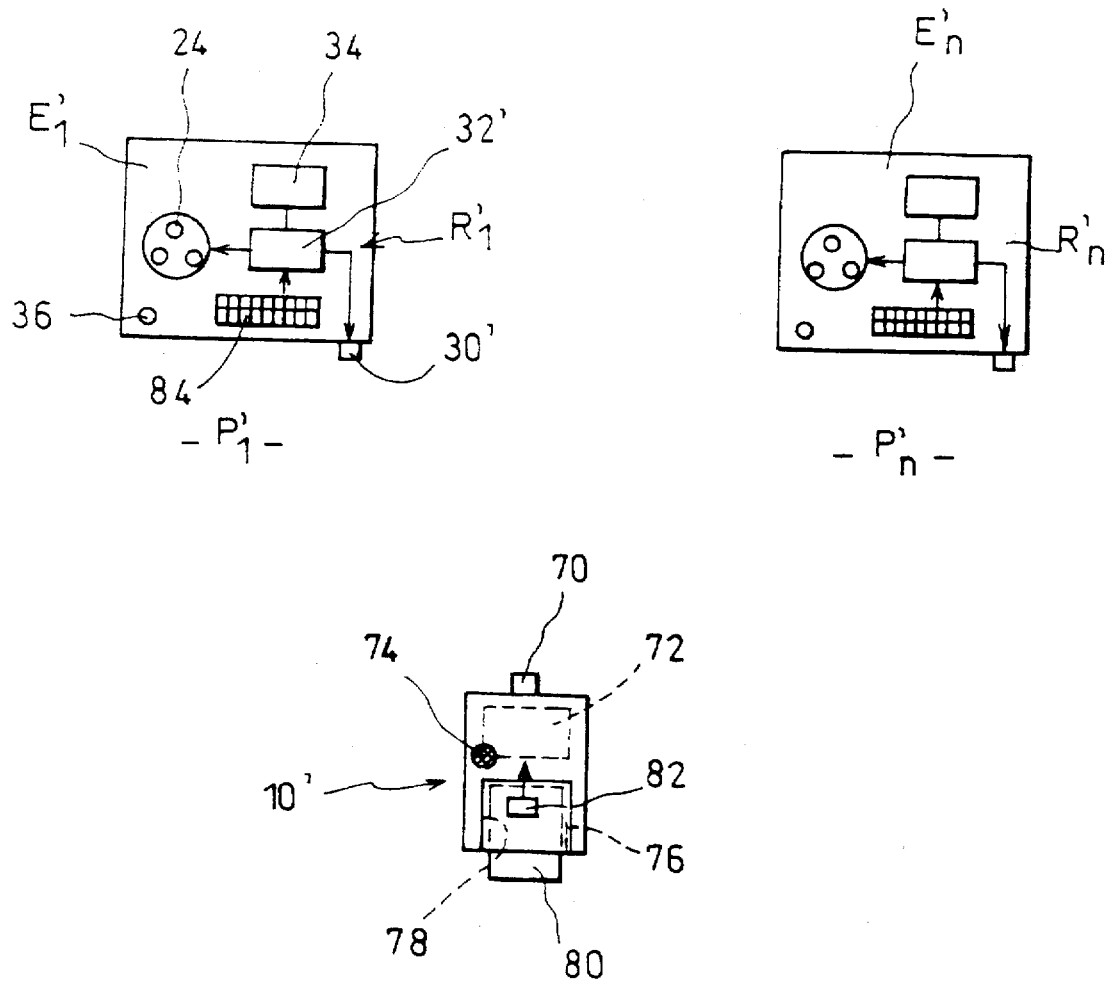
FIG_5

APPARATUS FOR REMOTELY MONITORING CONTROLLABLE DEVICES

BACKGROUND OF THE INVENTION

Field of the Invention

The present invention relates to an installation for remote monitoring of a plurality of controllable equipments, in particular equipments usable in hospitals, such as pumps for perfusion or for administering medication.

More precisely, the invention relates to an installation for remote and secure monitoring of equipments, in particular hospital equipments for administering liquids injectable into patients, which installation makes it possible simultaneously to verify continuously and remotely the modes of operation of said equipments and the operating stages thereof, and also, preferably but not necessarily, to control them remotely.

It will be understood that in a hospital, the various equipments to be verified, in particular pumps for administering medication, are situated in different premises and are intended for different patients, with a single person being responsible for verifying that they are operating properly. It is therefore advantageous to provide the person in charge of verifying operation of the equipments with means making it possible at all times to know the operating status of each of the equipments.

It is also possible for the possibility of access to controlling the equipment, optionally to modify the programming to be strictly limited to the person in charge of operation, or to be limited at least to a small number of authorized people.

In this type of remote control installation it is also desirable to be able, in the event of an error in programming or control of an equipment that has given rise to damaging consequences, e.g. for a patient, to know which particular person in the staff of the hospital is responsible for the wrong programming.

SUMMARY OF THE INVENTION

An object of the present invention is to provide a device for remote monitoring of a plurality controllable equipments, in particular equipment encountered in a hospital or the like, enabling progress in the operation of the equipments to be monitored continuously and remotely, and preferably ensuring that the possibility of programming or modifying the programming of the equipments is restricted to authorized people.

According to the invention, this object is achieved by an installation for remote monitoring of a plurality of controllable equipments which is characterized in that it comprises: a portable control device including:

means for memorizing at least a portion of the control information relating to each equipment in association with information identifying said equipment, said sequence of information including information representative of the operating duration of said equipment;

means for generating time information;

means for initializing the time information relative to said equipment effectively being controlled, thereby obtaining elapsed time information; and means for comparing said operating duration with the elapsed time information and for issuing an alarm signal as a function of the result of said comparison.

Preferably, the installation further includes means for authorizing a sequence of operating information to be input into an equipment only in response to a specific item of information.

It will be understood that by means of such a remote monitoring installation, any person responsible for using the equipments is continuously informed by the portable device he or she holds about the time during which an equipment or each equipment has been in operation and thus about the operating time remaining. Further, such people are informed when the equipment comes to the end of its operation, thereby enabling them to go and verify visually that the equipment has stopped and possibly take required action with the patient. It should also be specified that the term "information representative of the duration of equipment operation" should be understood as meaning either information concerning actual operating duration, e.g. for a pump, or else, e.g. for drip feed equipment, information concerning a volume to be administered which will have been converted to an equivalent time by an initial measurement of the operation of the drip feed equipment.

In a first embodiment, the control means of each equipment include means for transmitting the sequence of information for controlling operation and said portable device includes means for receiving said sequence of information.

In this embodiment, the equipments are controlled directly by the person responsible. The operation control information sequences are automatically transmitted to the portable device held by the person responsible and they are automatically memorized therein, thereby avoiding any risk of error.

In a second embodiment, the monitoring installation further includes:

a plurality of receiver devices for receiving said control information, each receiver device being mounted on a respective one of said equipments; said portable control device further including:

means for generating said sequence of information for controlling the operation of an equipment; and means for transmitting said sequence of control information to a receiver device; each receiver device comprising:

means for receiving said transmitted control information; and means for controlling said equipment as a function of said information.

In this second embodiment, the portable device serves firstly to transmit control information to the receiver devices associated with the equipments, and secondly to memorize said control information and to verify the operating duration of the equipment.

In a preferred embodiment, the control information sequence further includes information identifying the controlled equipment, and each receiver device further includes means for memorizing information identifying the equipment on which it is mounted, means for comparing the memorized identification information with the received identification information, and means for authorizing performance of at least some of the other information only if the two items of identification information correspond.

In a variant embodiment, the sequence of instructions further includes information identifying the portable control device, and each receiver device includes means for memorizing the identification information of the portable control device, means for comparing the memorized identification information with the identification information received subsequently, and means for performing at least some of said control information only if the two items of identification information correspond.

It will be understood that with these two preferred embodiments, it is possible to verify the insertion of operating information or of information for modifying operation into the control means of each equipment, thereby protecting the equipments against erroneous control instructions being inserted. In other words, they make it possible to authorize only a limited number of people to intervene on the operation of the controlled equipments.

Also in a preferred embodiment, each receiver device further includes transmitter means for re-transmitting at least a portion of the received control information sequence, and said portable control device includes means for receiving re-transmitted information, means for comparing the re-transmitted information with the transmitted information, and means for transmitting an acknowledge signal if the transmitted information and the re-transmitted information corresponds.

In this preferred embodiment, it can be seen that it is possible to ensure that the control information transmitted between the portable control device and the receiver devices associated with each equipment has been correctly decoded by the receiver devices of the equipments, thus naturally making it possible to eliminate any risk of error resulting from remote transmission of information sequences. This also makes it possible to initialize the counting down of operating time.

BRIEF DESCRIPTION OF THE DRAWINGS

Other characteristics and advantages of the present invention appear more clearly on reading the following description of several embodiments of the invention given as non-limiting examples. The description refers to the accompanying figures, in which:

FIG. 1 is a simplified outside view of a portable monitoring device;

FIG. 2 is a simplified view of a first embodiment of a remote monitoring and control installation;

FIG. 3 is a diagram showing the internal circuits of the FIG. 1 remote monitoring and control device;

FIG. 5 is a simplified view of another embodiment of an installation providing remote monitoring only.

DETAILED DESCRIPTION

Figure 4:
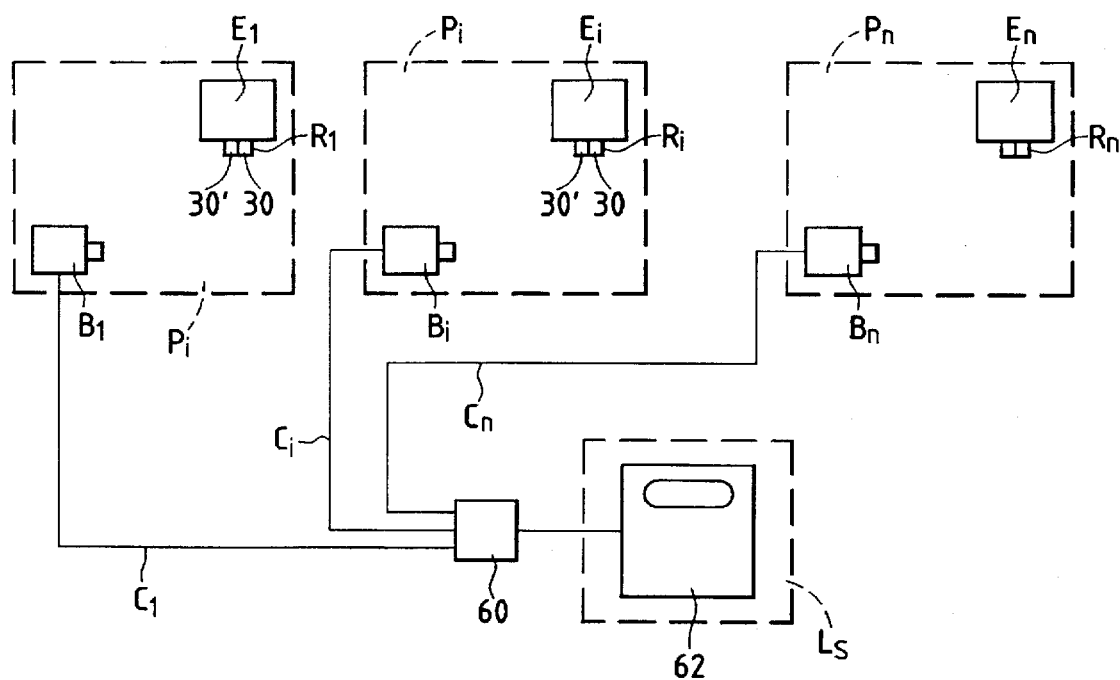
FIG. 4 shows a portion of a variant embodiment of a remote monitoring and control installation.

With reference initially to FIGS. 1 to 4, an embodiment of the invention is described which provides both remote monitoring and remote control of equipments.

With reference to FIG. 1, the outside appearance of the portable control device is described. This device is conventional in appearance, comprising a housing 10 which includes a transmitter of electromagnetic radiation and preferably of infrared radiation. The housing preferably further includes a receiver of radiation which may, for example, be the same as the transmitter. On its front face 14, the housing 10 has a display screen 16, e.g. a liquid crystal display, and a keypad 18 constituted by keys 20 enabling information to be input into the control device. The housing preferably also includes an alarm device 22 providing a sound and/or light and/or vibration alarm.

FIG. 2 is a diagram showing an entire remote control installation for equipments constituting a first embodiment. This installation has at least one control device 10 which is held by a person in charge of managing the operation of the equipments, and a plurality of equipments $E_1 \ldots E_n$ to be controlled and monitored. In the example shown, the equipments $E_1$ to $E_n$ are pumps, e.g. peristaltic pumps 24 having small wheels that are used for administering medication to a patient via tubing 26. In the embodiment, each equipment $E_i$ is installed in a ward $P_1 \ldots P_N$. Each equipment $E_i$ is provided with a control circuit 28 for the associated equipment and with a unit for receiving and processing operating information. Each receiver unit $R_1, R_2, \ldots$ essentially comprises an electromagnetic radiation receiver, preferably an infrared beam receiver 30 which is connected to a processor circuit 32, preferably associated with a re-writable memory 34. Each receiver unit $R_i$ may advantageously further comprise an infrared beam transmitter 30'. The processor circuit 32 is of conventional type and is capable of decoding the signals received by the detector 30 to transform them into instructions for controlling the operation of the equipment $E_1$ and thus for applying control signals to the control circuit 28 of the equipment. In addition, the equipment $E_1$ preferably includes a manual emergency stop member 36 which enables the operation of the equipment to be stopped when it is activated and in the absence of the remote control.

With reference now to FIG. 3, the various circuits of the control device 10 are described in greater detail, as are the various functions the device can implement. The circuit of the control device is essentially constituted, for example, by a microprocessor 40 associated firstly with a program memory 42 which may be an EEPROM type memory, for example, and secondly with a data memory 44 which, for example, is a RAM type memory or the like.

The microprocessor 40 can receive instructions issued by the user via the keypad 18. The decoder 46 converts the signals delivered by actuating the keys of the keypad into digital control signals that are directly usable by the microprocessor. The microprocessor 40 is also connected to an infrared beam transmit/receive cell 12. More precisely, the microprocessor 40 is connected to a control and encoding circuit 48 which controls emission by the diode 50 whenever it operates as a transmitter and which serves to perform analog-to-digital conversion of the signals received by the cell 50 whenever it operates as a receiver. The microprocessor is also connected to the display circuit 16 via an encoder circuit 52 that is well known per se. The circuits of the control device 10 also include a clock signal or time base 54 which delivers time pulses on an output 54a that are applied to an input 40a of the microprocessor 40. Finally, one of the outputs, preferably an analog output, of the microprocessor is connected to the audible alarm device 22.

There follows an explanation of how the control device 10 is used to program the operation of equipments $E_1 \ldots E_N$ associated with respective receiver devices $R_1 \ldots R_N$. To program an equipment, the holder of the control device 10 uses the keypad 18 to enter operating instructions for the equipment that is to be controlled. This sequence of instructions necessarily includes information representative of operating duration which may be constituted, as already explained, by actual duration information or by information concerning a volume to be administered, and preferably includes information for identifying the controlled equipment and information that identifies the control device. This sequence of information may also include instructions concerning the operating rate of the equipment when it is constituted by a pump, or other operating instructions. These instructions are received by the microprocessor 40 which causes them to be displayed in succession on the display circuit 16 so that the user can check visually that they are right.

In response to these instructions, the microprocessor causes the instructions to be recorded in the data memory 44 and it activates the control circuit 48 so that the infrared transmitter 50 transmits a coded signal representative of the various instructions. The infrared signal is received by the receiver 30 of the equipment $E_1$ to be controlled. The control circuit 32 of the equipment which is essentially constituted by a microprocessor, preferably causes the transmitter 30' to re-transmit the sequence of instructions as received back to the control device. This re-transmitted information is received by the detector 50 and the microprocessor checks that the transmitted information matches the received information. If there is a match, it causes the transmitter 50 to transmit an acknowledge signal to the equipment $E_1$. On reception of the acknowledge signal, the processor circuit 32 of the equipment conveys to the control circuit 28 the operating instructions for the equipment, e.g. the associated pump 24.

In a variant, it is possible to provide two procedures making it possible to ensure that the instructions conveyed are conveyed legally, i.e. by an authorized person. In a first verification mode, the memory 34 associated with the processor circuit 32 includes information specific to the equipment. The processor circuit 32 compares said information with the corresponding information in the control information sequence received from the control device 10. When there is a match, the instructions are indeed conveyed to the control circuit 28 of the associated equipment. In a verification variant, the memory circuit 34 includes an instruction for identifying the control device and the information sequence transmitted by the portable device 10 also includes identification information. The processor circuit 32 compares the two items of identification information and the instructions for controlling operation of the equipment are not performed unless the two items of identification information match.

When the control device transmits the acknowledge signal, the microprocessor 40 is caused to execute a time countdown subprogram which serves to compare the time information provided by the time base 54 with the instructed operating duration of the equipment as stored in the memory 44 in association with information identifying the equipment. When the comparison subprogram detects that the time which has actually elapsed has become equal to the operating duration of the equipment, the microprocessor 40 causes the alarm device 22 to be excited. In a variant embodiment, it is possible to provide for the comparison subprogram to generate a first comparison signal when the elapsed time corresponds to the programmed operating duration minus a predetermined pre-alarm duration stored in the memory 42, which duration may be equal to 5 minutes, for example. On detecting the pre-alarm instant, the component 22 transmits a special signal to inform the user that the equipment concerned $E_1$ will shortly come to an end of its operation. The equipment is identified in the memory of the portable device by a ward number, a bed number, a pump number, etc.

The above-described installation for remote control of equipment presents numerous advantages over manual control of said equipment.

The person responsible for managing a set of equipments and who holds the portable control device can find out at any time what the operating parameters are of each of the equipments he or she is in charge of, since these parameters are stored in the memory of the device. They can therefore be modified, where appropriate, by using the device to transmit new values for the parameters to the equipment concerned. In particular, it is possible to establish at any time the operating duration that remains for each equipment. In addition, the person responsible is automatically informed whenever an equipment has ceased to operate.

Because of the information identifying the control device and the equipments, it is possible to authorize the holder of a given control device to act only on a given equipment, or more likely on a given group of equipments.

Finally, since the operating instructions for the equipments remain in the memory of the control device, in the event of a problem it is possible to find out who gave the operating instructions, since that person will be the holder of the control device in the corresponding time period. In addition, by passing the portable device to another nurse, the other nurse has available, and without risk of error, all of the information relating to the equipments she is taking charge of.

FIG. 4 shows an improved embodiment of a remote control installation in a first embodiment. In the figure, there can be seen equipments $E_i$ with respective receiver devices $R_i$, each receiver device being provided with an infrared receiver 30 and an infrared transmitter 30'. Each equipment $E_i$ is installed in a ward $P_i$. Each ward $P_i$ is fitted with an infrared receiving terminal $B_i$ capable of receiving the infrared signals transmitted by the transmitter 30' of the equipment $E_i$. Each terminal $B_i$ is connected by an electrical conductor $C_i$ to a concentrator 60 which is in turn connected to a remote monitoring desk 62 installed in a monitoring room LS. In this embodiment, the circuits 28 and 32 of the receiver devices $R_i$ are configured to cause the transmitter 30' to transmit an infrared alarm signal in the event of faulty operation of the equipment with which it is associated. This alarm signal is received by the terminal $B_i$ and is conveyed to the remote monitoring desk 62.

In the simplified embodiment shown in FIG. 5, that serves to perform remote monitoring only of the equipments, the installation comprises at least one remote monitoring appliance 10' and a plurality of equipments $E'_1$ to $E'_n$ to be monitored that are installed in respective wards $P'_1 \ldots P'_n$. The monitoring appliance 10' is simplified compared with the monitoring and control appliance 10. It essentially comprises an electromagnetic signal receiver, preferably for receiving infrared signals, said receiver being referenced 70. The receiver 70 is connected to circuits inside the appliance and given general reference 72. These circuits 72 are explained below with reference to the diagram of FIG. 3. The appliance also includes an alarm device 74 which may provide an alarm that is optical, audible, or by means of vibration. The appliance preferably also defines a card reader 76, the reader essentially including a card insertion slot 78, and when the card 80 is of the electronic memory type, a connector 82 which is connected to the circuit 72. Naturally, the card could be of the magnetic type, for example, in which case the reader corresponds thereto. The card essentially contains in its memory information for identifying each person who may be in charge of the installation. When the card is inserted in the reader 76, the circuit 72 reads the information identifying the holder, which information is stored in the memory portion of the circuit 72. As explained below, this makes it possible to associate each set of operating information for an equipment $E'_i$ with information identifying the person who programmed the equipment.

Each equipment E' comprises, for example, a pump 24 associated with control and processing circuits 32' and with a memory 34, which unit forms the receiver device $R'_i$. To control the pump 24, each equipment includes an information input member, e.g. a keypad 84 which serves to input instructions for controlling the operation of the pump 24. When the person responsible has finished inputting information for controlling the operation of the pump 24, the processor circuit 32' controls a transmitter 30', e.g. an infrared transmitter, to cause it to send signals to the receiver 70 of the monitoring device 10' corresponding to all of the sequence of control information previously input by the person responsible.

The installation for remote monitoring is used as follows: when the person responsible seeks to program an equipment, e.g. the equipment $E'_1$, that person inserts the card 80 into the housing of the portable device 10' and uses the keypad 84 to input instructions for controlling the operation of the pump 24. These instructions are stored in the memory 34 and they are processed by the processor circuits 32'. When the person responsible has confirmed the sequence of instructions, the processor device 32' causes the infrared transmitter 30' to transmit a signal representative of the various instructions input together with information identifying the equipment. The portable device 10' is disposed in such a manner that its receiver 30 receives these signals. The processor circuit 72 converts these signals into digital data which is stored in a portion of the memory of the circuit 72. The information stored in the memory has the identification information as read from the card 80 added thereto. Thus, after successively controlling a plurality of equipments $E'_i$, the memory of the portable device 10' contains sets of information each including the identity of the equipment, the identity of the person responsible, and the instructions for controlling the operation of the corresponding equipment. The circuit 72 includes elements analogous to those shown in FIG. 3 for generating information relating to the time that has elapsed since said data was input into the portable device, which corresponds to the beginning of operation of the corresponding equipment, and means for comparing the time that has elapsed since said initialization with information representative of the programmed operating duration for the equipment. The circuits 72 include components which control the alarm device 74 when the operating duration has been reached or possibly, as already explained above with reference to the preceding figures, which issues a pre-alarm signal followed by an alarm signal.

It should be added that with the portable device 10 of the first embodiment described with reference to FIGS. 1 to 4, it is also possible to provide for the portable device to include a magnetic or electronic card reader integrated in its housing and into which the person responsible must insert a card to enable the control and monitoring device 10 to operate.

Although particular embodiments of the invention have been described in detail for purposes of illustration, various changes and modifications may be made without departing from the scope and spirit of the invention. Accordingly, the invention is not to be limited except as by the appended claims and their equivalents.

I claim:

1. A remotely monitored installation comprising:
    a plurality of controllable equipment, each of said equipment including control means activated in response to a control information sequence, said control information including information concerning duration of operation, said control means comprising means for transmitting the sequence of control information for controlling the operation; and
    a portable control device held by a person responsible for controlling said equipment by inputting at least said control information sequence, said portable control device comprising:
    memorizing means;
    means for receiving said sequence of control information from said equipment and for storing at least a portion of said sequence of control information in said memorizing means, whereby at least a portion of the control information relating to each of said equipment in association with information identifying said equipment are memorized, said memorized information including at least the information representative of the operating duration of said equipment;
    means for generating time information;
    means for initializing the time information to a time base related to each of said equipment being controlled, thereby obtaining elapsed time information measured from the initial time base;
    means for comparing said operating duration with the elapsed time information; and
    means for issuing an alarm signal as a function of the result of said comparison.

2. A remotely monitored installation according to claim 1, further including means for authorizing a sequence of operating information to be input into an equipment only in response to verified identification information.

3. An installation according to claim 1, characterized in that said control information sequence further includes information identifying the controlled equipment, and in that each receiver device further includes means for memorizing information identifying the equipment on which it is mounted, means for comparing the memorized identification information with the received identification information, and means for authorizing performance of at least some of the other information only if the two items of identification information correspond.

4. An installation according to claim 3, characterized in that it includes a plurality of equipment, a plurality of receiver devices, and a plurality of portable control devices, each receiver device including means for memorizing a plurality of items of portable control device identification information and means for authorizing performance of at least some received control information if the identification information of the control device that transmitted said information is stored in said receiver device.

5. An installation according to claim 1, characterized in that said portable device further includes means for reading information identifying the user of the portable device and stored in a removable information medium, and means for memorizing said user identification information together with the sequence of information for controlling the operation of an equipment.

6. A remotely monitored installation comprising:
    a plurality of controllable equipment, each of said equipment comprising:
    control means activated in response to a control information sequence, said control information including information concerning duration of operation and input by a person responsible for monitoring and controlling said equipment;
    a receiver device associated with each of the equipment for receiving said control information;
    means for transmitting said received control information to said control means; and
    a portable control device held by the person responsible for monitoring said equipment condition, said portable control device comprising:

means for generating said sequence of control information for controlling the operation of each of said equipment;

means for transmitting said sequence of control information to the receiver device;

memorizing means for memorizing at least a portion of the sequence of the control information relating to each of said equipment in association with information identifying each of said equipment, said sequence of memorized information including at least the information representative of the operation duration of said equipment;

means for generating time information;

means for initializing the time information to a time base related to each of said equipment being controlled, thereby obtaining elapsed time information measured from the initial time base;

means for comparing said operating duration with the elapsed time information; and means for an issuing an alarm signal as a function of said comparison.

7. A remotely monitored installation according to claim 6, further including means for authorizing a sequence of operating information to be input into said equipment only in response to verified identification information.

8. An installation according to claim 6, characterized in that said sequence of instructions further includes information identifying the portable control device, and in that each receiver device includes means for memorizing the identification information of the portable control device, means for comparing the memorized identification information with the identification information received subsequently, and means for performing at least some of said control information only if the two items of identification information correspond.

9. An installation according to claim 6, characterized in that each receiver device further includes transmitter means for re-transmitting at least a portion of the received control information sequence, and in that said portable control device includes means for receiving re-transmitted information, means for comparing the re-transmitted information with the transmitted information, and means for transmitting an acknowledge signal if the transmitted information and the re-transmitted information corresponds.

10. An installation according to claim 9, characterized in that said acknowledge signal received by said portable control device initializes the means for generating time information relating to the equipment which transmitted the acknowledge signal.

11. An installation according to claim 6, characterized in that said information is transmitted in the form of electromagnetic waves.

12. An installation according to claim 11, characterized in that said information is transmitted in the form of an infrared signal.

13. An installation according to claim 11, characterized in that said portable control device comprises a housing with a keypad, a display device, means for transmitting an electromagnetic wave, and electronic circuits for generating said information on the basis of data input via the keypad, for storing said information, and for controlling the means for transmitting the electromagnetic wave as a function of the generated information.

14. An installation according to claims 11, characterized in that each receiver device device further includes means for transmitting information relating to the actual operation of the equipment on which said receiver device is mounted, and in that said installation further includes at least one terminal suitable for receiving said information about actual operation and for forwarding it to a monitoring center.

15. An installation according to claim 6, characterized in that said portable control device further includes means for programming time duration information, and in that said means for transmitting an alarm signal includes means for transmitting a pre-alarm signal at an instant that precedes the operating duration of at least one of the equipments by a length of time equal to a programmed time duration programmed by said means for programming time duration information.

* * * * *